United States Patent
Obayan

(10) Patent No.: US 10,799,622 B2
(45) Date of Patent: *Oct. 13, 2020

(54) REDUCING POST-OPERATIVE ADHESION FORMATION WITH INTRAPERITONEAL GLUTAMINE

(71) Applicant: AdeTherapeutics Inc., Saskatoon, Saskatchewan (CA)

(72) Inventor: Adebola O. E. Obayan, Saskatoon (CA)

(73) Assignee: Ade Therapeutics, Inc., Saskatoon, Saskatchewan (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/180,637

(22) Filed: Nov. 5, 2018

(65) Prior Publication Data

US 2019/0111189 A1    Apr. 18, 2019

Related U.S. Application Data

(63) Continuation of application No. 15/480,148, filed on Apr. 5, 2017, now abandoned, which is a continuation of application No. 14/660,382, filed on Mar. 17, 2015, now abandoned, which is a continuation of application No. 13/779,362, filed on Feb. 27, 2013, now Pat. No. 9,011,883, which is a continuation of application No. 12/063,423, filed as application No. PCT/CA2006/001319 on Aug. 11, 2006, now abandoned.

(60) Provisional application No. 60/707,173, filed on Aug. 11, 2005.

(51) Int. Cl.
| | | |
|---|---|---|
| A61K 38/05 | (2006.01) | |
| A61P 41/00 | (2006.01) | |
| A61L 31/14 | (2006.01) | |
| A61L 31/16 | (2006.01) | |
| A61K 9/00 | (2006.01) | |
| A61K 9/12 | (2006.01) | |
| A61L 31/04 | (2006.01) | |
| A61K 31/198 | (2006.01) | |
| A61L 31/10 | (2006.01) | |

(52) U.S. Cl.
CPC ............ *A61L 31/16* (2013.01); *A61K 9/0019* (2013.01); *A61K 9/0024* (2013.01); *A61K 9/12* (2013.01); *A61K 31/198* (2013.01); *A61K 38/05* (2013.01); *A61L 31/047* (2013.01); *A61L 31/10* (2013.01); *A61L 31/145* (2013.01); *A61L 31/148* (2013.01); *A61L 2300/214* (2013.01); *A61L 2300/25* (2013.01); *A61L 2300/252* (2013.01); *A61L 2300/412* (2013.01); *A61L 2300/424* (2013.01)

(58) Field of Classification Search
CPC .... A61K 31/198; A61K 38/05; A61K 9/0019; A61K 9/0024; A61K 9/12; A61L 2300/214; A61L 2300/25; A61L 2300/252; A61L 2300/412; A61L 2300/424; A61L 31/047; A61L 31/10; A61L 31/145; A61L 31/148; A61L 31/16

See application file for complete search history.

(56) References Cited

U.S. PATENT DOCUMENTS

| | | | |
|---|---|---|---|
| 5,171,837 A | 12/1992 | Tanihara et al. | |
| 5,425,740 A * | 6/1995 | Hutchinson, Jr. | ..... A61B 17/122 227/902 |
| 5,693,671 A | 12/1997 | Niihara et al. | |
| 5,795,584 A | 8/1998 | Totakura et al. | |
| 6,063,061 A | 5/2000 | Wallace et al. | |
| 6,280,745 B1 | 8/2001 | Flore et al. | |
| 6,613,070 B2 | 9/2003 | Redmond et al. | |
| 6,638,949 B1 | 10/2003 | Folkman et al. | |
| 6,797,729 B1 | 9/2004 | Byrne et al. | |
| 6,965,014 B1 | 11/2005 | Delmotte et al. | |
| 9,011,883 B2 * | 4/2015 | Obayan | ................ A61K 31/198 424/400 |
| 2002/0004037 A1 | 1/2002 | Koteliansky et al. | |
| 2002/0013298 A1 * | 1/2002 | Hunter | ................ A61K 9/0014 514/113 |
| 2003/0007951 A1 | 1/2003 | Franklin et al. | |
| 2005/0070484 A1 | 3/2005 | Neu et al. | |

FOREIGN PATENT DOCUMENTS

| | | |
|---|---|---|
| CA | 2501540 | 4/2004 |
| EP | 0549660 | 6/1999 |
| EP | 0904071 | 11/2000 |

(Continued)

OTHER PUBLICATIONS

Gere diZerega (Peritoneal Surgery; Springer Science & Business Media: 2000, p. 218). 1 page (Year: 2000).*

(Continued)

*Primary Examiner* — Ernst V Arnold

(74) *Attorney, Agent, or Firm* — Brinks Gilson & Lione

(57) ABSTRACT

The present disclosure relates to a method of treating or reducing adhesions in the peritoneum of a patient in need thereof. The method includes performing adhesiolysis on one or more adhesions involving the patient's peritoneum and/or one or more tissues or organs in the patient's peritoneal cavity; and administering to the peritoneum or the peritoneal cavity of the patient an effective amount of a composition comprising at least one glutamine source. The glutamine source is selected from one or more of L-glutamine, physiologically acceptable salts of L-glutamine, and dipeptides comprising L-glutamine.

9 Claims, No Drawings

(56) References Cited

FOREIGN PATENT DOCUMENTS

| WO | WO 00/06120 | 2/2000 |
|---|---|---|
| WO | WO 2004/032653 | 4/2004 |
| WO | WO 2005/030242 | 4/2005 |
| WO | WO 2007/016791 | 2/2007 |

OTHER PUBLICATIONS

"A0550 Ala-Gin" from Sigma-Aldrich and enlarged images, 2 pages, partially downloaded Dec. 21, 2004 from website http://www.sigmaaldrich.com/cgibin/hsrun/Suite7/Suite. hjx; start=Su ite. HsView . . . .

Ackermann, et al. "Microcirculation of the Rat Omentum Studied by Means of Corrosion Casts," Aca Anat, vol. 140, pp. 146-149, 1991.

"Adhesion Products" from International Adhesion Society, 2 pages, downloaded Jan. 13, 2005 from website https://www.adhesions.org/products.htm.

Adibi, et al. "Removal of Glycylglutamine from Plasma by Individual Tissues: Mechanism and Impact on Amino Acid Fluxes in Postabsorption a Starvation," J. Nutr., vol. 123, Supplement 2, pp. 325-331, Feb. 1993, Abstract Only.

"Ajinomoto Develops New Peptide Manufacture Method," press release dated Nov. 29, 2004, 1 page, downloaded Dec. 21, 2004 from website http://www.ift.org/news_bin/news/newsBody.shtml.

"Alanyl-Glutamine Dipeptide Enriched Plants and Seeds," Patent Foundation University of Virginia, 1 page, downloaded Jan. 6, 2005 from website http://www.uvaof.ora/technoloaieslindex.cfm/fuseaction/inventionlinvention id/274I?CF . . . .

Ardawi, et al., Glutamine metabolism in lymphocytes of the rat, Biochem. J., 1983, vol. 212, pp. 835-842.

Askanazi, et al. "Muscle and Plasma Amino Acids after Injury: Hypocaloric Glucose vs. Amino Acid Infusion" Annals of Surgery, vol. 191, No. 4, pp. 465-472, Apr. 1980.

Babst, et al. "Glutamine Peptide-Supplemented Long-Term Total Parenteral Nutrition: Effects on Intracellular and Extracellular Amino Acid Patterns, Nitrogen Economy, and Tissue Morphology in Growing Rats," Journal of Parenteral and Enteral Nutrition, vol. 17, No. 6, pp. 566-574, Nov.-Dec. 1993.

Bae, et al. "Comparison of Intraperitoneal Anti-Adhesive Polysaccharides Derived from Phellinus Mushrooms in a Rat Peritonitis Model," World Journal of Gastroenterology, vol. 11, No. 6, pp. 810-816, 2005.

Bakkum, et al. "Quantitative Analysis of the Inflammatory Reaction Surrounding Sutures Commonly Used in Operative Procedures and the Relation to Postsurgical Adhesion Formation," Biomaterials, vol. 16, pp. 1283-1289, 1995.

Baykal, et al. "Effects of Polyglycolic Acid and Polypropylene Meshes on Postoperative Adhesion Formation in Mice," World J. Surg, vol. 21, pp. 579-583, 1997.

Bridges, et al. "Peritoneal Adhesion Formation," Acta Anat., vol. 61, pp. 203-212, 1965.

Cardona, Pera D., "Administration of Glutamine and its Dipeptides in Parenteral Nutrition. Which Patients are Candidates?," Nut. Hosp, vol. 13, No. 1, pp. 8-20, Jan.-Feb. 1998.

Cranshaw, et al. "Milky Spots of the Omentum: A Source of Peritoneal Cells in the Normal and Stimulated Animal," Arch. Histol. Cytol., vol. 43, Supplement, pp. 165-177, 1990.

Dijkstra, et al. "Recent Clinical Developments in Pathophysiology, Epidemiology, Diagnosis and Treatment of Intra-abdominal Adhesions," Scand J Gastroenterol, Supplement 232, pp. 52-59, 2000.

Doruk, et al. "The Effect of Preventive Use of Alanyl-Glutamine on Diaphragm Muscle Function in Cecal Ligation and Puncture-Induced Sepsis Model," Journal of Parenteral and Enteral Nutrition, vol. 29, No. 1, pp. 36-43, Jan.-Feb. 2005.

Drollette, et al. "Pathophysiology of Pelvic Adhesions," The Journal of Reproductive Medicine, vol. 37, No. 2, pp. 107-122, 1992.

Dux, Kazimierz. "Proliferative Activity of Macrophages in the Greater Omentum of the Mouse in Relation to the Early Postnatal Development of the Vascular Structures," Journal of Leukocyte Biology, vol. 40, pp. 445-458, 1986.

Ellis, Harold, "The Causes and Prevention of Intestinal Adhesions," British Journa/ of Surgery, vol. 69, No. 5, pp. 241-243, 1982.

Ellis, Harold. "The Clinical Significance of Adhesions: Focus on Intestinal Obstruction," Eur. J. Surg 163, Supplement 577, pp. 5-9, 1997.

"Emulsion/Suspension Stabilizers and Thickeners," product information from R.T. Vanderbilt Company, Inc., 4 pages, downloaded Jan. 19, 2005 from website http://www.rtvanderbilt.com/specialties 7.htm.

"FDA Approves Controversial Surgical Gel," 2 pages, downloaded on Jan. 13, 2005 from website http://www.usatoday.com/news/health/2001-11-19-disputed-drug.htm.

"Fibrin Sealant Demonstrates Reduced Comp from Breast Cancer Surgery," press release, downloaded Jan. 13, 2005 from website http:/www.pslgroup.com/dg/3df72.htm.

Fuentes-Orozco, Clotilde et al., L-alanyl-L-glutamine-supplemented parenteral nutrition improves infectious morbidity in secondary peritonitis, Clinical Nutrition, vol. 23, Issue 1, pp. 13-21, Feb. 2004.

Fukuzawa, et al. "N-Acetylcysteine Ameliorates Reperfusion Injury After Warm Hepatic Ischemia," Transplantation, vol. 59, No. 1, pp. 6-9, Jan. 15, 1995.

"Functions of Glutamine," The Society of Hospital Pharmacists of Hong Kong, downloaded Jan. 6, 2005 from website http://www.shphk.gor.hklindex.php?option=com content&task=view&id=196 &Itemid=- . . . .

Fürst, et al. "Availability of Glutamine Supplied Intravenously as Alanylglutamine," Metabolism, vol. 38, No. 8, Supplement 1, pp. 67-72, Aug. 1989.

"G8541 Ala-Gin" from Sigma-Aldrich, 1 pages, downloaded Dec. 21, 2004 from website https://www.sigmaaldrich.com/cgi-bin/hsrun/Suite7/Su ite/Su ite. hjx; start=Su ite. HsView . . . .

Gadallah, et al. "Relationship Between Intraperitoneal Bleeding, Adhesions, and Peritoneal Dialysis Catheter Failure: A Method of Prevention," Advances in Peritoneal Dialysis, vol. 17, pp. 127-129, 2001.

"Gel Heals Wounds Without Scars," dated Oct. 26, 2000, product information Confluent Surgical, downloaded Jan. 13, 2005 from website http://www.confluentsurgical.com/bbcoct.htm.

"Glutamine Peptides," PDRhealth, Informed Consent, downloaded Jan. 6, 2005 from website http://www.pdrhealth.com/drug info/nmdrugprofiles/nutsupdrugs/glu 0124.shtml.

Gorman, Jessica. "Beyond Jell-O: New Ideas Gel in the Lab," Science News, downloaded Jan. 13, 2005 from website http://www.phschool.com/science/science news/articles/beyond jello.html.

Gynecare Interceed (TC7), product information, 2 pages, downloaded from www.gynecare.com.

Gynecare Interceed (TC7), product information, 2 pages, downloaded Jan. 13, 2005 from website http://www.gynecare.com/bgdisplay.jhtml?itemname-interceed about.

"Gynecare Intergel" Final Product Labeling, Lifecore Biomedical, Inc., distributed by Gynecare, a division of Ethicon, Inc., 11 pages.

"Gynecare Intergel" New Device Approval, CDRH Consumer Information, 2 pages, downloaded Jan. 13, 2005 from website http://www.fda.gov/cdrg/mda/docs/P990015.html.

Harris, et al., "Open pore biodegradable matrices formed with gas foaming", J. Biomed. Mater. Res. (1998). 42:396-402.

Hayashi, Yoshitaka,et al. "Preoperative Glutamine Administration Induces Heat-Shock Protein 70 Expression and Attenuates Cardiopulmonary Bypass-induced inflammatory response by regulating nitric oxide synthase activity", Circulation, 2002, p. 2601-2607, vol. 106.

Heil, et al., "Species-specific recognition of single-stranded RNA via Toll-like receptor 7 and 8", Science (2004).303:1526-1529.

Hershlag, Avner et al. "The Effect of Interleukin-1 on Adhesion Formation in the Rat", Am. J. Obstet. Gynecol., pp. 771-774, vol. 165, 1991.

Holmdahl, et al. "The Role of Cytokines, Coagulation, and Fibrinolysis in Peritoneal Tissue Repair," Eur. J. Surg., vol. 165, pp. 1012-1019, 1999.

International Search Report dated Nov. 15, 2006.

(56) References Cited

OTHER PUBLICATIONS

Ivarsson, et al. "Tissue Markers as Predictors of Postoperative Adhesions," British Journal of Surgery, vol. 85, pp. 1549-1554, 1998.
Jiang, Z.-M. "Modifications of Parenteral Nutrition Support for Critical Surgical Illness," 6 pages, downloaded Jan. 6, 2005 from website http://www.unu.edu/unupress/food2/UID07E/uid07e1 g.htm.
Karner, et al. "Influence of Alanylglutamine Infusion on Gastrointestinal Glutamine and Alanine Metabolism in Anesthetized Dogs," Metabolism, vol. 38, No. 8, Supplement 1, pp. 73-77, Aug. 1989.
Lacey, et al. "Is Glutamine a Conditionally Essential Amino Acid?," Nutrition Reviews, vol. 48, No. 8, pp. 297-309, Aug. 1990.
Leach, et al. "Photocrosslinkable Hyaluronic Acid Hydrogels for Tissue Engineering," Mat. Resc. Soc. Symp. Proc., vol. EXS-1, pp. F4.7.1-F4.7.3, 2004.
Liakakos, et al. "Peritoneal Adhesions: Etiology, Pathophysiology, and Clinical Significance," Digestive Surgery, vol. 18, pp. 260-273, 2001.
Luijendijk, et al. "Foreign Material in Postoperative Adhesions," Annals of Surgery, vol. 223, No. 3, pp. 242-248, 1996.
Matsukawa, et al. "Endogenous Monocyte Chemoattractant Protein-1 (MCP-1) Protects Mice in a Model of Acute Septic Peritonitis: Cross-Talk between MCP-1 and Leukotriene B4," The Journal of Immunology, vol. 163, pp. 6148-6154, 1999.
Menzies, Donald, "Peritoneal Adhesions—Incidence, Cause, Prevention," Surg. Annu. Surg., vol. 24, pp. 27-45, 1992.
Menzies, et al. "Intestinal Obstruction from Adhesions—How Big is the Problem'?," Annals of the Royal College of Surgeons of England, vol. 72, pp. 60-63, 1990.
Miller, Alan L. "Therapeutic Considerations of L-Glutamine: A Review of the Literature," 12 pages, downloaded Jan. 6, 2005 from website http://www.thorne.com/altmedrev/fullItexUglutamine4-4.html.
Morlion, et al. Total Parenteral Nutrition with Glutamine Dipeptide after Major Abdominal Surgery. A Randomized, Double-Blind, Controlled Study, Annals of Surgery, vol. 227, No. 2, pp, 302-208, 1998.
"Myodrive" product information from Netrition, Inc., 4 pages, downloaded on Jan. 6, 2005, from website http://www.netrition.com/san myodrive page.html.
Naim, et al. "Reduction of Postoperative Adhesions to Marlex Mesh using Experimental Adhesion Barriers in Rats," Journal of Laparoendoscopic Surgery, vol. 3, No. 2, pp. 187-190, 1993.
Newsholme, E.A. "The Possible Role of Glutamine in Some Cells of the Immune System and the Possible Consequence for the Whole Animal," Experientia, vol. 52, pp. 455-459, 1996.
Newsholme, et al. "Glutamine Metabolism in Lymphocytes: Its Biochemical, Physiological and Clinical Importance," QJ Exp. Physiol., vol. 70, pp. 473-489, 1985.
Newsholme, et al. "The Role of High Rates of Glycolysis and Glutamine Utilization in Rapidly Dividing Cells," Bioscience Reports, vol. 15, pp. 393-400, 1985.
Nordfjeld, K. et al., Storage of mixtures for total parenteral nutrition-long-term stability of a total parenteral nutrition mixture., Journal of Clinical and Hospital Pharmacy, vol. 8, pp. 265-274, 1983.
Obayan, A. O.E., Oxidative Stress: Natural History and Modulation in Surgery and Trauma Patients (Dissertation for Degree of Doctor of Philosophy), University of Saskatchewan, Summer 2004, 202 pages.
Parker, et al. "Postoperative Adhesions: Ten-Year Follow-Up of 12,584 Patients Undergoing Lower Abdominal Surgery," Dis Colon Rectum, vol. 44, No. 6, pp. 822-829, Jun. 2001.
Pata, Oezlem et al., "The effect of inducible nitric oxide synthase on postoperative adhesion formation in rats", European Journal of Obstetrics and Gynecology and Reproductive Biology, 2004, p. 64-69, vol. 117.
"Pharmaceutical Ingredients Information ", 1 pages, downloaded Jan. 19, 2005 from website http://www.grainprocessing.com/pharm/pharminfo. html.

"Product Catalog" of Parchem., 2 pages, downloaded Jan. 19, 2005 from website https"//www.parchem.com/Product.aspx?ClassName=organic.
Pucciarelli, et al. Effect of Antiadhesive Agents on Peritoneal Carcinomatosis in an Experimental Model, British Journal of Surgery, pp. 66-71, downloaded Dec. 21,2004 from website http://www.bis.co.uklbisCda/cdalmicroJournalArticleDetail.do?DOI=1 0.1 002%2fbis.4 . . . , Abstract only.
Pytlik, et al. "Standardized Parenteral Alanyl-Glutamine Dipeptide Supplementation is not Beneficial in Autologous Transplant Patients: A Randomized, Double-Blind, Placebo Controlled Study," Bone Marrow Transplant, vol. 30, No. 12, pp. 953-961, Dec. 2002, Author's comment in vol. 33, No. 4, p. 455, Feb. 2004.
Ray, et al. "Abdominal Adhesiolysis: Inpatient Care and Expenditures in the United States in 1994," J Am Coll Surg, vol. 186, No. 1, pp. 1-9, Jan. 1998.
Robinson, et al. eds., "Controlled Drug Delivery: Fundamentals and Applications", 2nd ed. vol. 29 Marcel Dekker, Inc. New York. 1987. p. 5.
Rodgers, et al. "Function of Peritoneal Exudate Cells after Abdominal Surgery," Journal of Investigative Surgery, vol. 6, pp. 9-23, 1993.
Rosiak, et al. "Radiation Formation of Hydrogels for Biomedical Applications," Institute of Applied Radiation Chemistry, Technical University of Lodz Wroblewskiego 15, 93-590 Lodz, Poland, The International Atomic Energy Aaencv's report © 2002, Centre of Excellence "Lasers & Biomaterials in Medicine" report © 2002, 50 pages.
Roth, E. "Changes in Protein Metabolism in Cachexia and Catabolism," Z. Exp Chir Transplant Kunstliche Organe., vol. 18, No. 3, pp. 150-156, 1985.
Roth, et al. "Liver Amino Acids in Sepsis," Surgery, vol. 97, No. 4, pp. 436-442, Apr. 1985.
Sallah, et al. "Glutamine Metabolism in Lymphocytes of the Rat," Biochem. J., vol. 212, pp. 835-842, 1983.
Satoh, et al. "Enteral Alanyl-Glutamine Supplement Promotes Intestinal Adaptation in Rats," International Journal of Molecular Medicine, vol. 12, pp. 615-620, 2003.
Satoh et al., Nutritional benefects of enteral alanyl-glutamine supplementation on rat small intestinal damage induced by cyclophosphamide., Journal of Gastroenterology and Hepatology, 2003, vol. 18, pp. 719-725.
"Seprafilm" Drugs Approved by the FDA, 1 page, downloaded on Jan. 13, 2005 from website http://www.centerwatch.com/patientldrugs/DRU155.html.
"Sizing & Thickening Agents," Fredonia Study #1544, New US Industry Study, 4 pages, May 2002.
Shimotsuma, et al. "Cellular Subsets of the Milky Spots in the Human Greater Omentum," Cell and Tissue Research, vol. 264, pp. 599-601, 1991.
Shimotsuma, et al. "Milky Spots in the Human Greater Omentum," Acta Anat., vol. 136, pp. 211-216, 1989.
Shimotsuma, et al. "Ontogeny of Milky Spots in the Fetal Lamb Omentum," Arch. Histol. Cytol., vol. 57, No. 3, pp. 291-299, 1994.
Smith, Robert J. "Glutamine Metabolism and Its Physiologic Importance," Journal of Parenteral and Enteral Nutrition, vol. 14, No. 4, Supplement, pp. 40S-44S, Jul.-Aug. 1990.
Takemori, N. "Morphological Studies of the Omental Milk Spots in the Mouse: Light and Electron Microscopy," Hokkaido Igaku Zasshi, vol. 54, No. 3, pp. 265-283, 1979.
"The Clinical Significance of the Role of Glutamine in Immune Cells," 5 pages, downloaded on Jan. 6, 2005 from website http://www.unu.edu/unupress/food2/UID07E/uid07e1 c.htm.
"There's a New Way to Avoid Internal Scars After Surgery," 2 pages, product information downloaded Jan. 13, 2005 from website http://www.confluentsurgical.com/newscientific.htm.
Thompson, et al. Pathogenesis and Prevention of Adhesion Formation, British Journal of Surgery, vol. 82, pp. 3-5, 1995.
Thompson, J.N. "Preventing Adhesions," The Lancet, vol. 346, p. 1382, Nov. 25, 1995.
Tigerman, Henry, et al., Glutamine, Glutamic Acid, Ammonia Administration and Tissue Glutamine, 1951, pp. 793-799.

(56) References Cited

OTHER PUBLICATIONS

"Total Parenteral Nutrition:" 3 pages, downloaded on Jan. 18, 2005 from website http://www.nlm. nih.gov/medlineplus/druginfo/medmaster/a601166.html.
"Triblock Poly(lactide)-poly(ethylene oxide}-poly(lactide) Hydrogels: Structure and Mechanical Properties," Sarvesh K. Agrawal, speaker, AIChE Conference, 2 pages, dowloaded Jan. 13, 2005 from website http://www.aiche.ora/conferences/technroaram/paperdetail.asp?PaperID=1223&DSN=a . . . .
Valente, et al. "Mechanisms in Intimal Monocyte-Macrophage Recruitment," Circulation, vol. 86, No. 6, Supplement III, pp. 111-20-111-25, Dec. 1992.
Van Zaanen, et al. "Parenteral Glutamine Dipeptide Supplementation Does Not Ameliorate Chemotherapy-Induced Toxicity," Cancer, vol. 74, No. 10, pp. 2879-2884, Nov. 15, 1994, Abstract Only.
Vinnars, et al. "Influence of the Postoperative State on the Intracellular Free Amino Acids in Human Muscle Tissue," Annals of Surgery, vol. 182, No. 6, pp. 665-671, Dec. 1975.
Vipond, et al. "Peritoneal Fibrinolytic Activity and Intra-abdominal Adhesions," The Lancet, vol. 335, pp. 1120-1122, May 12, 1990.
Vural, et al. "The Role of Neutrophils in the Formation of Peritoneal Adhesions," Human Reproduction, vol. 14, No. 1 , pp. 49-54, 1999.
Ward, et al. "Oral Glutamine in Paediatric Oncology Patients: A Dose Finding Study," European Journal of Clinical Nutrition, vol. 57, pp. 31-36, 2003.
Werb, et al. "Plasma Membrane Synthesis in the Macrophage Following Phagocytosis of Polystyrene Latex Particles," The Journal of Biological Chemistry, vol. 247, No. 8, pp. 2439-2446, 1972.
Whawell, et al. "Cytokine-Induced Release of Plasminogen Activator Inhibitor-1 by Human Mesothelial Cells," Eur J Surg, vol. 161, pp. 315-317, 1995.
Williams, et al. "The Greater Omentum: Applicability to Cancer Surgery and Cancer Therapy," Curr Probl Surg. vol. 23, No. 11, pp. 789-865, Nov. 1986.
Wikipedia, Peritoneum, accessed Sep. 22, 2014, pp. 1-7.
Wischmeyer, et al. "Single Dose of Glutamine Enhances Myocardial Tissue Metabolism, Glutathione Content, and Improves Myocardial Function After Ischemia-Reperfusion Injury," Journal of Parenteral and Enteral Nutrition, vol. 27, No. 6, pp. 396-403, Nov.-Dec. 2003, Abstract only,.
Wiseman, David. "Prevention of Post-Surgical Adhesions," OBGYN. net Chat, 4 pages, downloaded Jan. 13, 2005 from website http://www.obgyn.neUchat callWiseman chat 0819.htm.
Yang, Rongjie, et al. "Alanine-Glutamine dipeptide (AGD) Inhibits expression of inflammation-related genes in hemorrhagic shock", Journal of Parenteral and Enteral Nutrition, pp. 32-36, vol. 31, No. 1, 2007.
Zühlke, et al. "Pathophysiology and Classification of Adhesions," Langenbecks Arch Chir Suppl II Verh Dtsch Ges Chir., pp. 1009-1016, 1990.
Dipeptiven, Online Medicine, accessed Sep. 13, 2016, pp. 1-3.

* cited by examiner

REDUCING POST-OPERATIVE ADHESION FORMATION WITH INTRAPERITONEAL GLUTAMINE

CROSS-REFERENCE TO RELATED APPLICATIONS

This application is a Continuation application of U.S. patent application Ser. No. 15/480,148, filed Apr. 5, 2017; which is a Continuation application of U.S. patent application Ser. No. 14/660,382, filed Mar. 17, 2015, now abandoned; which is a Continuation application of U.S. patent application Ser. No. 13/779,362, filed Feb. 27, 2013, now issued as U.S. Pat. No. 9,011,883; which is a Continuation application of U.S. patent application Ser. No. 12/063,423, filed Feb. 8, 2008, now abandoned; which is a National Stage application of International Application No. PCT/CA2006/001319, filed Aug. 11, 2006; which claims the benefit of U.S. Provisional Application No. 60/707,173, filed Aug. 11, 2005, the entire contents of which are hereby incorporated herein by reference.

BACKGROUND OF THE INVENTION

Adhesions are abnormal deposits of fibrous tissue that form within the peritoneal cavity. Abdominal adhesions are a common cause of small bowel obstruction and female infertility [1-3]. Adhesion formation occurs after any surgical procedure. However, it is extremely common after abdominal and pelvic operations and remains a source of considerable morbidity. The incidence ranges from about 67%-93% after general surgical abdominal operations and up to about 97% after open gynecologic pelvic procedures [4, 5]. In clinical and autopsy studies of patients who had prior laparotomy, the incidence of intra-abdominal adhesions was about 70-90% [6]. Use of both absorbable polyglycolic acid meshes and non-absorbable polypropylene meshes as reinforcing materials in surgery is associated with a high incidence of adhesion formation [6a, 6b].

Factors associated with the formation of post-surgical adhesions include trauma, thermal injury, infection, ischemia and foreign bodies. Other factors associated with adhesion formation include tight suturing where tension within the sutured peritoneum produces ischemia and abrasion. Exposure to foreign bodies such as talc and powders from the gloves, lint from abdominal packs or disposable papers items may also contribute to the formation of adhesions [7-9]. Neutropenia is associated with lower rates of adhesion and may play a role in modulating post-operative adhesion [10].

The peritoneum is composed of two mesothelial sheets that enclose predominantly adipocytes embedded in loose connective tissue, and also aggregates of mononuclear phagocytic cells. The greater omentum is the largest part of the peritoneum with the size varying from 300 gm to 2000 gm and a surface area of 300 $cm^2$ to 1500 $cm^2$. The omentum has a rich vascular supply with numerous characteristic capillary convolutions that are termed omental glomeruli due to their similarity with renal glomeruli. These capillary beds lie directly under the mesothelium [11]. Adhesions are formed as a result of fibrous repair of peritoneal injury mostly after surgery.

Milky spots develop as specific structures in the greater omentum of the peritoneum between the 20th and 35th week of gestation [12]. They are corpuscles found in the omental glumeruli measuring 0.1-2 mm in size, hardly visible to the naked eye, and under low magnification look like tufts of cotton wool [13, 14]. Milky spots are characterized by a permanent glomus pattern of vascular structure, specific cellular population and a specialized mesothelial lining. In humans, milky spots comprise of macrophages (70%), B-lymphocytes (10%), T-lymphocytes (10%), mast cells, and stromal cells. The mean number of cells in one milky spot is approximately 600 [15]. The number of milky spots is highest in infancy and gradually decreases with age [12]. The activation of milky spot, which occurs within 6 hours of abdominal surgery plays a role in adhesion formation [16].

The macrophages in the mature omentum are essentially scavengers. They appear to differentiate from monocytic precursors in the milky spots and are not dependent on precursors derived from the bone marrow [17]. They are dendritic in shape and have marked phagocytic abilities. They avidly phagocytose intraperitoneally injected carbon particles and bacteria. When activated, the macrophage precursors in the milky spots proliferate, migrate to the mesothelial surface, and transform into dendritic-shaped macrophages. Following surgery, macrophages increase in number and change function which are different from the resident macrophages and secrete variable substances including cycloxygenase and lipoxygenes metabolites, plasminogen activator, plasminogen activator inhibitor (PAI) etc. [9, 18]. These macrophages recruit new mesothelial cells that proliferate forming islands in the injured areas resulting in peritoneal remesothelialization. Following stimulation of the milky spot there is an increased microvascular permeability to fluid, neutrophils, monocytes and fibrin deposits within the connective tissue matrix of milky spots, and subsequent increased cellular migration across the mesothelial lining into the peritoneal cavity [19].

Adhesion formation begins with injury inflicted on the peritoneum whether by an injurious stimuli including bacterial, chemical toxicity, ischemia, mechanical or simply drying from exposure [16, 25]. The injury leads to an inflammatory response, which progresses to fibrin deposition and subsequent fibrinous adhesion. If the fibrinous adhesion is not degraded within the first days of injury, reparative cells including fibroblasts are propagated into the fibrin matrix turning it into permanent fibrous adhesion. This process is completed within a week of the injury. The balance of fibrin deposition and breakdown is therefore crucial in the early phase of peritoneal repair and adhesion formation [25-27]. Peritoneal macrophages may be involved in regulation of plasmin activity in the peritoneal cavity [28], and thus a role in adhesion formation [29].

Various methods of adhesion prevention and treatment have been employed, including prevention of fibrin deposition in the peritoneal exudate, reduction of local tissue inflammation, and removal of fibrin deposits. Most of the existing methods inhibit one of these categories and yet have limited success. Implants in the form of resorbable fabrics or membranes (which are thought to act as macrophage barriers) as well as gels formed of biocompatible materials have also been employed to reduce formation of adhesions. Examples are the products sold under the trademarks INTERCEED and SEPRAFILM.

Glutamine is a conditional essential amino acid which the body is unable to synthesize in sufficient quantities under certain physiologic circumstances [30, 31] such as major surgery, shock, traumatic injury and severe sepsis. A decrease in extracellular glutamine impairs the function of macrophages and other immune cells, resulting in increased protein degradation from skeletal muscle [20]. Macrophages are extremely active cells (10 times per minute based on ATP turnover and 5 times a minute based on oxygen consumption) with a high capacity to take up glutamine and 'trap it' as glutamate, which acts as an intracellular store for both energy formation and provision of precursors for biosynthesis. Mouse peritoneal macrophages have been shown to utilize a high amount of glutamine via the process of glutaminolysis even though they are seen as terminally differentiated cells [21, 22]. These macrophages are characterized by high rate of protein secretion and membrane recycling [23, 24]. Although glutamine constitutes >50% of the unbound amino acid pool in human skeletal muscle, rapid reduction in blood and tissue glutamine has been noted following catabolic events such as major surgery [32], trauma [33], and sepsis [34, 35].

Glutamine is safe, well absorbed, and has no documented side effects. Glutamine is known to enhance wound healing. Glutamine and its dipeptides have been used for parenteral and enteral supplementation components in critically ill patients. A recent study by Fukuzawa, et al. [36] concluded that glutamine enhances both phagocytosis and the production of Reactive Oxygen Intermediates (ROI) by neutrophils in post-operative patients. In a randomized prospective study, Morlion et al. using glutamine dipeptides in total parenteral nutrition (TPN) concluded that the supplement group had shorter hospital stay, improved immune status and nitrogen balance after abdominal surgery [37].

Alanyl-glutamine and glycyl-glutamine are two dipeptides of glutamine which have been employed clinically due to their higher solubility and chemical stability over free glutamine, making them more stable sources of the constituent amino acids [37-42]. Enteral supplementation with alanyl-glutamine but not glutamine+alanine mixture promotes intestinal adaptation as evidenced by increased peptide transport after intestinal resection [43]. Alanyl-glutamine also prevents intestinal damage, as demonstrated by increased peptide transport expression and an elevated plasma glutamine concentration after CPM administration [44]. Alanyl-glutamine alone was recently used enterally in post-operative patients for the first time with reported success and safety [53].

SUMMARY OF THE INVENTION

We have found that intraperitoneal administration of a glutamine source will reduce post-operative adhesion formation. This is surprising because glutamine is a direct fuel for macrophages. In view of the presumed role of macrophages derived from activated milky spots in peritoneal repair and adhesion formation, one may expect that glutamine could exacerbate the formation of adhesions. While we do not wish to be bound to a particular line of reasoning with respect to an underlying mechanism pertaining to this invention, we believe that intraperitoneal administration of glutamine enhances peritoneal repair without assistance of macrophages derived from activated milky spots.

Alanyl-glutamine and L-glutamine are effective in reducing and/or preventing post-operative adhesions (including secondary adhesions) when administered intra-peritoneally. This effect is not prevented by the presence of intraperitoneal bleed, suture type, or degree of inflammation. Presently, it appears the effect of alanyl-glutamine is more pronounced than that of L-glutamine in adhesion prevention.

Previous therapies involving glutamine administration have employed either enteral administration (e.g. in a food supplement) or parenteral administration through the intravenous route (e.g. administration of a total parenteral nutrition formulations). As a result of this invention, it will now be known to be advantageous to employ intraperitoneal administration of a glutamine source for patients undergoing or having undergone a surgical procedure that affects the peritoneum. Furthermore, this invention may be facilitated through use of formulations that act as a glutamine source and are thickened so as to have a greater viscosity than formulations which are suitable for intravenous injection. This will facilitate directed placement of the formulation within the peritoneal cavity and adherence to selected areas. Such thickened formulations must be sterile and otherwise suitable for intraperitoneal administration and thus are different from glutamine containing formulations previously used for enteral feeding.

A glutamine source may be administered directly to the peritoneum or within the peritoneal cavity and may also be applied to implants and/or medical devices which are placed within the peritoneum. Examples of such implants or medical devices include woven resorbable material or mesh and other barriers or shields currently used or proposed for use as means to reduce surgical adhesions. A particularly preferred formulation for use in this invention is a gel or a mesh containing an aqueous phase in which a glutamine source is dissolved.

In a first aspect, this invention provides a composition for intraperitoneal administration comprising a pharmaceutically acceptable carrier and at least one glutamine source. Such a composition is useful for treatment of a patient to reduce post-operative adhesion formation. The composition may be placed on or impregnated in a surgical material or an implantable medical device. The composition may be present in a delivery device suitable for delivery of the composition intraperitoneally during surgery.

In another aspect, this invention provides use of a glutamine source for reducing post-operative adhesion formation.

In another aspect, this invention provides use of a glutamine source in the manufacture of a medicament for intraperitoneal administration to reduce post-operative adhesion formation.

In another aspect, this invention provides a method of treating a patient to reduce post-operative adhesion formation comprising intraperitoneal administration of an effective amount of a glutamine source to said patient.

Various embodiments of this invention provide a sterile composition for use in reducing post-operative adhesions comprising a glutamine source and a pharmaceutically acceptable carrier suitable for intraperitoneal administration. The composition may comprise one or more pharmaceutically/physiologically acceptable diluents and excipients, including thickeners or other viscosity enhancing agents. Preferably, a viscosity enhancing agent will form a gel when hydrated. Such compositions may comprise simply a water soluble glutamine source and a suitable gel forming agent in dry form. The latter formulation may also be provided in a partially hydrated or fully hydrated form.

This invention also provides a device suitable for performing intraperitoneal administration of a glutamine containing formulation. The device may be adapted for intraperitoneal administration of the formulation in a variety of known ways, including by injection or other extrusion process, dropping or spraying and may take the form of a syringe, bellows container, squeezable container, pressure operated spray apparatus and the like.

DETAILED DESCRIPTION OF THE INVENTION

In this specification, the term "glutamine source" includes L-glutamine and its physiologically acceptable salts, as well as peptides comprising L-glutamine. While L-glutamine may be employed in this invention, this amino acid has a relatively low water solubility (36 g/L at 20° C.) and tends to break down during sterilization and prolonged storage. Oligopeptides comprising L-glutamine which are capable of being metabolized to provide L-glutamine may also be employed in this invention. Preferably, such peptides will exhibit increased solubility in water over that of L-glutamine. Often, such peptides will also exhibit increased resistance to breakdown during sterilization and storage. Two such peptides that may be used in this invention are dipeptides comprising L-glutamine and either L-alanine or glycine. The dipeptide alanyl-glutamine (glutamine residue at the C-terminal position) has high solubility in water (568 g/L). Glycyl-glutamine (glutamine at the C-terminal position) also shows enhanced solubility in water as compared to glutamine (154 g/L). Each of the latter dipeptides is sufficiently stable during heat sterilization and prolonged storage that they have been previously employed in total parenteral nutrition formulations for intravenous injection.

Pharmaceutically acceptable preparations of L-glutamine and L-glutamine containing peptides (including alanyl-glutamine) are commercially available. In addition, L-glutamine containing peptides for use in this invention may also be synthesized according to known methodology and purified and sterilized for pharmaceutical use.

Compositions of this invention may be in dry, partially hydrated, or fully hydrated form and will include a glutamine source plus a pharmaceutically acceptable carrier or diluent component such as sterile distilled water, sterile isotonic solutions, sterile physiological saline solutions or dry buffer and/or salt mixes or concentrations which when diluted form such a solution. The quantity of the glutamine source in the composition will be selected in order to provide for a fully solublized amino acid or peptide during administration. Further, the quantity of L-glutamine available from the composition when formulated for administration and/or total amount of formulation administered will be selected by the skilled medical provider in order to provide a suitable dose of L-glutamine to the patient.

Based on previous studies involving intravenous administration of L-glutamine and its dipeptides, an intraperitoneal dose may provide from about 0.01 g to about 1.0 g of L-glutamine per patient kilogram, per day. However, doses may be selected to fall outside these upper and lower amounts. Typical doses employing alanyl-glutamine may be the range of about 0.1 g to about 0.5 g of the dipeptide/kg/day.

When administering a glutamine source during a surgical procedure, the typical dose for an average adult human patient may provide from about 0.3 g to about 2.0 g or about 0.3 g to about 1.5 g of L-glutamine or alanyl-glutamine within the peritoneal cavity.

Administration according to this invention may involve delivery of a glutamine source to the peritoneal cavity during surgery, at the end of surgery before closure, or soon after closure. This invention also contemplates subsequent, post-operative intraperitoneal and/or intravenous administration of a glutamine source by injection.

Formulations for use in this invention may be a liquid, paste, or gel comprising a glutamine source dissolved in an aqueous phase. Compositions of this invention may be such formulations or may be compositions intended to produce such a formulation when hydrated. In its simplest form, a formulation for use in this invention will consist of a glutamine source dissolved in a sterile aqueous liquid vehicle, suitable for instilling within the peritoneal cavity during surgery or for intraperitoneal injection performed thereafter. The solution may be instilled during surgery simply by injection, depositing, or spraying it into the peritoneal cavity from a suitable sterile container. The formulation may be instilled through a port created for laparoscopic surgery.

Particularly suitable formulations for use in this invention will be thickened in order that the formulation will exhibit increased viscosity over a typical liquid formulation suitable for intravenous injection. Such thickened formulations will be in the form of a paste or gel which may be applied directly to selected tissues or regions of the peritoneum or within the peritoneal cavity during a surgical procedure. Suitable pharmaceutically acceptable thickening agents are known and may be employed. Preferably, such an agent will form a hydrogel when hydrated or will form a hydrogel when subjected to a suitable cross-linking agent and is hydrated. Such gel forming components are selected for their biocompatibility and may be resorbable. Examples of suitable thickeners and gel forming agents which have been employed in pharmaceutical formulations include polymers having a hydrophilic component, such as collagen; polyoxyalkylene polymers such as polyethylene oxides, polyvinyl alcohols, polyvinyl pyrrolidones, and polyhydroxyethyl methacrylates; hyaluronates; and various proteins such as albumin, etc. Hemostatic gels, including those which contain fibrinogen or fibrin may also be used.

A glutamine source may also be applied to or impregnated in surgical implants. For example, a gel formulation of this invention may be adhered to the exterior of an implant. Implants composed of a material such as woven resorbable cellulose (such as the kind as is sold under the trademark INTERCEED) may be impregnated with a liquid or gel formulation of this invention.

EXAMPLE 1

70 plus male Wistar rats (over 350 g each) were assessed histologically on post-operative days 1,3,5,7,10, 30, and at about 6 weeks. The rats were randomly distributed based on the mode of treatment, type of sutures and presence or absence of hemorrhage during surgery. Initially, there were three surgery groups (alanyl-glutamine treatment, saline, no treatment) plus a control (no surgery). A fifth group using L-glutamine instead of alanyl-glutamine was included after preliminary results were obtained.

The rats were anaesthetized with halothane/Ketamine. Open surgery involving a midline sub-umbilical incision and a modified cecal puncture with pulstring to prevent soilage after abdominal closure was done. The procedure involved some fecal extrusion, mimicking clinical scenarios of iatrogenic/traumatic perforations of the bowel. Alanyl-glutamine [Degussa; Coubevoie, France] (0.3 g/kg-1.5 g/kg); saline (5 ml); or L-glutamine [Wiler; PCCA] (1.5 g/kg) was instilled into the peritoneal cavity from a syringe. The cecum, abdomen, and the skin were closed in layers using the same suture. Various absorbable (3/0 Vicryl™, 3/0 Monocryl™, 3/0 PDS™, 2/0 Maxon™) and non-absorbable sutures (3/0 Prolene™, 3/0 Ethibond™, 4/0 & 5/0 Surgilene™, 3/0 Novafil™) were used. The wound was infiltrated with local anesthetic. The animals were given sufficient chow to eat (20 g/day≈2 mmole/kg/day). The gastrointestinal tract and omentum were harvested from the stomach to the sigmoid colon and fixed in formaldehyde solution for evaluation.

The severity of adhesions was assessed histologically using standard Haematoxylin & Eosin and Masson trichrome stained slides. The latter helped delineate the degree of fibrosis and collagen deposition.

Semi-quantitative analysis was done by scoring the average number of milky spots per high-power-field (HPF). Quantitative statistical analysis was done using the T-test between the experimental groups. Milky spots are a marker for inflammation and adhesion formation. We found that more milky spots were associated with more adhesion formation.

On the $10^{th}$ post-operative day, the histological appearance of the peritoneum in alanyl-glutamine treated rats had very minimal adhesion when compared with the untreated and the saline treated surgical groups and was almost comparable to the virgin (control) rat peritoneum. This result continued in rats assessed at 6 weeks. There was 1 milky spot per 5 high power field (5HPF) in the peritoneum of the controls in comparison with 6-7 milky spots per SHPF in the untreated surgical group. The milky spots in the alanyl-glutamine treatment group were the same as the controls while the saline treated group had 2-4 milky spots per SHPF.

Results also revealed markedly reduced amount of acute inflammatory response in the days 3-7 (alanyl-glutamine) treatment group in comparison with the saline and non-treatment surgical groups. This was evident by the reduced amount of macrophages and macrophage chemotactic proteins. L-glutamine treatment also resulted in reduction, but to a lesser extent than in the alanyl-glutamine treated group. There was also reduced fibrosis and collagen deposition in the day-10 animals in the treatment versus saline and non-treatment surgical groups. However, saline treatment showed better results than the non-treatment surgical group.

The dosage of alanyl-glutamine was effective at 0.3 g/kg and at 1.5 g/kg. There was more adhesion from the braided sutures (3/0 Vicryl™, 2/0 Maxon™, 3/0 Dexon™ & 3/0 Ethibond™) than the non-braided or monofilaments (3/0 Monocryl™, 3/0 PDS™, 3/0 Prolene™, 4/0 & 5/0 Surgilene™, 3/0 Novafil™) in the non-treated and saline-treated groups. There also appeared to be differential tendencies towards adhesion formation with the monofilament sutures (absorbable versus non-absorbable sutures). However, alanyl-glutamine treatment prevented adhesions in all the suture groups.

Some previous human studies used parenteral doses of alanyl-glutamine ranging from 0.19-0.75 g/kg/day [42, 47]. Rats have been given 2.972 g/kg/day alanyl-glutamine and 2.0 g/kg/day L-glutamine (mixed with 1.22 g/kg/day alanine) enteral bolus supplement [43]. In the present example, we administered 0.3-1.5 g/kg alanyl-glutamine and L-glutamine intraperitoneally. We did not observe complications due to the intraperitoneal use of alanyl-glutamine or L-glutamine as the rats recovered from surgery and continued with their usual activities.

We evaluated macrophage activity following the abdominal surgery using a macrophage chemotactic protein (MCP1) antibody stain. MCP1 is a marker for macrophage activity [46]. Our observation of reduced MCP1 in the glutamine source treatment groups as compared with the saline and non-treatment surgical groups indicated that the glutamine source treatment had an inhibitory effect on microphage migration following abdominal surgery. The fact that MCP1 was reduced by the treatment but was not completely absent is significant since complete absence is not desirable as it is associated with peritonitis and septic complications post-laparotomy [48].

Peritoneal suturing increases ischemia, devascularization, and necrosis thereby predisposing to adhesion formation [49]. Monofilaments have been shown to produce less adhesion than braided sutures because their micropores have a tendency to harbour bacteria [50, 51]. We observed a similar pattern in the untreated rats. However, the treatment prevented adhesions in all suture groups.

Hemorrhage is also associated with increased incidence of adhesion even with the use existing prevention therapies. Intraperitoneal bleeding causes intense inflammatory reactions and extensive adhesions and its relationship with adhesions is well documented in both animal and human studies [52]. We observed that hemorrhage did not prevent the effect of the treatment.

EXAMPLE 2

Previous studies show a high incidence of adhesion formation when surgical mesh is employed as a reinforcing material [6a, 6b]. We repeated trials as described in Example 1, inserting Marlex™ mesh during the procedure on the surgical groups. Comparable results to that described in Example 1 were obtained between days 1-42.

Severity of adhesions was assessed at day 90 using the adhesion score of Zuhlke, et al. [54]. This scoring procedure has been described in the literature for assessment of other potential treatments for adhesions [55]. At day 90, the adhesion score in animals treated with alanyl-glutamine was 0-1 (no adhesion or flimsy adhesion), comparable to the virgin abdomens of the control group. This differs from previous measurements of adhesions using polypropylene mesh which reported up to about 90% adhesion formation [6a].

EXAMPLE 3

Adhesions tend to recur once in place. We examined the effect of alanyl-glutamine treatment on such secondary adhesions. The modified caecal perforation with pulstring closure procedure described in Example 1 was performed on 9 Sprague-Dawley rats. These were divided into 5 groups, each group receiving a different form of mesh (INTERCEED™; PROCEED™; BARD™ composite; prolene; and a mesh which was allowed to be "infected" by repeated re-opening of the wound). The surgical procedure with mesh implacement was performed without application of a glutamine source. Six months after initial surgery, a laparotomy was performed on each rat then adhesiolysis followed by installation of alanyl-glutamine. Three weeks later the rats were assessed for recurrence of adhesions and scored according to Zuhlke, et al. [54] and no secondary adhesions were seen.

Although the foregoing invention has been described in some detail by way of illustration and example for purposes of clarity of understanding, it will be readily apparent to those of skill in the art in light of the teachings of this invention that changes and modification may be made thereto without departing from the spirit or scope of the appended claims. All patents, patent applications and publications referred to herein are hereby incorporated by reference.

REFERENCES

1. Thompson, J. N. and S. A. Whawell, Pathogenesis and prevention of adhesion formation. Br J Surg, 1995.82(1): p. 3-5.
2. Thompson, J. N., Preventing adhesions. Lancet, 1995.346 (8987): p. 1382.

3. Ellis, H., The clinical significance of adhesions: focus on intestinal obstruction. Eur J Surg Suppl, 1997(577): p. 5-9.
4. Menzies, D. and H. Ellis, Intestinal obstruction from adhesions—how big is the problem? Ann R Coll Surg Engl, 1990. 72(1): p. 60-3.
5. Parker, M. C., et al., Postoperative adhesions: ten-year follow-up of 12,584 patients undergoing lower abdominal surgery. Dis Colon Rectum, 2001. 44(6): p. 822-29; discussion 829-30.
6. Ellis, H., The causes and prevention of intestinal adhesions. Br J Surg, 1982. 69(5): p. 241-3.
6a. Naim, J. o., et al., J. Laparoendosc Surg, 1993. 3: p. 187-90.
6b. Baykal, A., et al., World J Surg, 1997.21: p. 579-82.
7. Menzies, D., Peritoneal adhesions. Incidence, cause, and prevention. Surg Annu, 1992. 24 Pt 1: p. 27-45.
8. Bridges, J. B., F. R. Johnson, and H. W. Whitting, Peritoneal adhesion formation. Acta Anat (Basel), 1965. 61(2): p. 203-12.
9. Drollette, C. M. and S. Z. Badawy, Pathophysiology of pelvic adhesions. Modern trends in preventing infertility. J Reprod Med, 1992. 37(2): p. 107-21; discussion 121-2.
10. Vural, B., et al., The role of neutrophils in the formation of peritoneal adhesions. Hum Reprod, 1999. 14(1): p. 49-54.
11. Ackermann, P. C., P. D. De Wet, and G. P. Loots, Microcirculation of the rat omentum studied by means of corrosion casts. Acta Anat (Basel), 1991. 140(2): p. 146-9.
12. Shimotsuma, M., et al., Ontogeny of milky spots in the fetal lamb omentum. Arch Histol Cytol, 1994. 57(3): p. 291-9.
13. Takemori, N., [Morphological studies of the omental milk spots in the mouse: light and electron microscopy (author's transl)]. Hokkaido Igaku Zasshi, 1979. 54(3): p. 265-83.
14. Shimotsuma, M., et al., Milky spots in the human greater omentum. Macroscopic and histological identification. Acta Anat (Basel), 1989. 136(3): p. 211-6.
15. Shimotsuma, M., et al., Cellular subsets of the milky spots in the human greater omentum. Cell Tissue Res, 1991. 264(3): p. 599-601.
16. Williams, R. and H. White, The greater omentum: its applicability to cancer surgery and cancer therapy. CUIT Probl Surg, 1986.23(11): p. 789-865.
17. Dux, K., Proliferative activity of macrophages in the greater omentum of the mouse in relation to the early postnatal development of the vascular structures. J Leukoc Biol, 1986. 40(4): p. 445-58.
18. Rodgers, K. E. and G. S. diZerega, Function of peritoneal exudate cells after abdominal surgery. J Invest Surg, 1993. 6(1): p. 9-23.
19. Cranshaw, M. L. and L. V. Leak, Milky spots of the omentum: a source of peritoneal cells in the normal and stimulated animal. Arch Histol Cytol, 1990. 53 Suppl: p. 165-77.
20. Newsholme, E. A., The possible role of glutamine in some cells of the immune system and the possible consequence for the whole animal. Experientia, 1996. 52(5): p. 455-9.
21. Newsholme, E. A., B. Crabtree, and M. S. Ardawi, The role of high rates of glycolysis and glutamine utilization in rapidly dividing cells. Biosci Rep, 1985. 5(5): p. 393400.
22. Newsholme, E. A., B. Crabtree, and M. S. Ardawi, Glutamine metabolism in lymphocytes: its biochemical, physiological and clinical importance. Q J Exp Physiol, 1985. 70(4): p. 473-89.
23. Werb, Z. and Z. A. Cohn, Plasma membrane synthesis in the macrophage following phagocytosis of polystyrene latex particles. J Biol Chem, 1972. 247(8): p. 2439-46.
24. Ardawi, M. S. and E. A. Newsholme, Glutamine metabolism in lymphocytes of the rat. Biochem J, 1983. 212(3): p. 835-42.
25. Dijkstra, F. R., et al., Recent clinical developments in pathophysiology, epidemiology, diagnosis and treatment of intra-abdominal adhesions. Scand J Gastroenterol Suppl, 2000(232): p. 52-9.
26. Vipond, M. N., et al., Peritoneal fibrinolytic activity and intra-abdominal adhesions. Lancet, 1990. 335(8698): p. 1120-2.
27. Whawell, S. A. and J. N. Thompson, Cytokine-induced release of plasminogen activator inhibitor-1 by human mesothelial cells. Eur J Surg, 1995. 161(5): p. 315-8.
28. Holmdahl, L. and M. L. Ivarsson, The role of cytokines, coagulation, and fibrinolysis in peritoneal tissue repair. Eur J Surg, 1999. 165(11): p. 1012-9.
29. Ivarsson, M. L., et al., Tissue markers as predictors of postoperative adhesions. Br J Surg, 1998. 85(11): p. 1549-54.
30. Smith, R. J., Glutamine metabolism and its physiologic importance. JPEN J Parenter Enteral Nutr, 1990. 14(4 Suppl): p. 40S-44S.
31. Lacey, J. M. and D. W. Wilmore, Is glutamine a conditionally essential amino acid? Nutr Rev, 1990. 48(8): p. 297-309.
32. Vinnars, E., J. Bergstom, and P. Furst, Influence of the postoperative state on the intracellular free amino acids in human muscle tissue. Ann Surg, 1975. 182(6): p. 665-71.
33. Askanazi, J., et al., Muscle and plasma amino acids after injury: hypocaloric glucose vs. amino acid infusion. Ann Surg, 1980. 191(4): p. 465-72.
34. Roth, E., [Changes in protein metabolism in cachexia and catabolism). Z Exp Chir Transplant Kunstliche Organe, 1985. 18(3): p. 150-6.
35. Roth, E., et al., Liver amino acids in sepsis. Surgery, 1985. 97(4): p. 436-42.
36. Fukuzawa, K., et al., N-acetylcysteine ameliorates reperfusion injury after warm hepatic ischemia. Transplantation, 1995. 59(1): p. 6-9.
37. Morlion, B. J., et al., Total parenteral nutrition with glutamine dipeptide after major abdominal surgery: a randomized, double-blind, controlled study. Ann Surg, 1998. 227(2): p. 302-8.
38. Furst, P., S. Albers, and P. Stehle, Availability of glutamine supplied intravenously as alanylglutamine. Metabolism, 1989. 38(8 Suppl 1): p. 67-72.
39. Karner, J. and E. Roth, Influence of alanylglutamine infusion on gastrointestinal glutamine and alanine metabolism in anesthetized dogs. Metabolism, 1989. 38(8 Suppl 1): p. 73-7.
40. Babst, R., et al., Glutamine peptide-supplemented long-term total parenteral nutrition: effects on intracellular and extracellular amino acid patterns, nitrogen economy, and tissue morphology in growing rats. JPEN J Parenter Enteral Nutr, 1993. 17(6): p. 566-74.
41. Nordfjeld, K., M. Rasmussen, and V. G. Jensen, Storage of mixtures for total parenteral nutrition—long-term stability of a total parenteral nutrition mixture. J Clin Hosp Pharm, 1983. 8(3): p. 265-74.

42. Cardona Pera, D., [Administration of glutamine and its dipeptides in parenteral nutrition. Which patients are candidates?]. Nutr Hosp, 1998. 13(1): p. 8-20.
43. Satoh, J., et al., Enteral alanyl-glutamine supplement promotes intestinal adaptation in rats. Int J Mol Med, 2003. 12(4): p. 615-20.
44. Satoh, J., et al., Nutritional benefits of enteral alanyl-glutamine supplementation on rat small intestinal damage induced by cyclophosphamide. J Gastroenterol Hepatol, 2003. 18(6): p. 719-25.
45. Ray, N. F., et al., Abdominal adhesiolysis: inpatient care and expenditures in the United States in 1994. J Am Coll Surg, 1998. 186(1): p. 1-9.
46. Valente, A J., et al., Mechanisms in intimal monocyte-macrophage recruitment. A special role for monocyte chemotactic protein-l. Circulation, 1992. 86(6 Suppl): p. 11120-5.
47. Ward, E., et al., Oral glutamine in paediatric oncology patients: a dose finding study. Eur J Clin Nutr, 2003.57(1): p. 31-6.
48. Matsukawa, A., et al., Endogenous monocyte chemoattractant protein-1 (MCP-1) protects mice in a model of acute septic peritonitis: cross-talk between MCP-1 and leukotriene B4. J Immunol, 1999. 163(11): p. 6148-54.
49. Luijendijk, R. W., et al., Foreign material in postoperative adhesions. Ann Surg, 1996.223(3): p. 242-8.
50. Liakakos, T., et al., Peritoneal adhesions: etiology, pathophysiology, and clinical significance. Recent advances in prevention and management. Dig Surg, 2001. 18(4): p. 260-73.
51. Bakkum, E. A., et al., Quantitative analysis of the inflammatory reaction surrounding sutures commonly used in operative procedures and the relation to postsurgical adhesion formation. Biomaterials, 1995. 16(17): p. 1283-9.
52. Gadallah, M. F., et al., Relationship between intraperitoneal bleeding, adhesions, and peritoneal dialysis catheter failure: a method of prevention. Adv Perit Dial, 2001, 17: p. 127-9.
53. Obayan, A. O. E., Oxidative stress: Natural History and Modulation in Surgery and Trauma Patients. Ph.D. in Surgery Thesis, University of Saskatchewan, Spring 2004.
54. Zuhlke, H. V., et al., Langenbecks Arch Chir Suppl II Verh Dtsch Ges Chir, 1990. p. 1009-16.
55. Bae, J. S., et al., World J Gastroenterol 11: p. 810-816.

I claim:

1. A method of treating or reducing adhesions in the peritoneum of a patient in need thereof, comprising:
   (a) performing adhesiolysis on one or more adhesions involving the patient's peritoneum and/or one or more tissues or organs in the patient's peritoneal cavity; and
   (b) administering to the peritoneum or the peritoneal cavity of the patient an effective amount of a composition comprising at least one glutamine source;
   wherein the glutamine source is a dipeptide selected from alanyl-glutamine and glycyl-glutamine.

2. The method of claim 1, wherein the dipeptide is alanyl-glutamine.

3. The method of claim 1, wherein the glutamine residue of the dipeptide is at the C-terminus of the dipeptide.

4. The method of claim 3, wherein the glutamine residue is L-glutamine.

5. The method of claim 1, wherein the composition is selected from the group consisting of a liquid composition, a paste composition, and a gel composition.

6. The method of claim 5, wherein the liquid composition is a sterile aqueous composition.

7. The method of claim 1, wherein the composition is impregnated in a surgical material.

8. The method of claim 7, wherein the surgical material is a mesh.

9. The method of claim 5, wherein the gel composition is a hydrogel.

* * * * *